United States Patent
Hertwig et al.

(10) Patent No.: US 9,684,125 B2
(45) Date of Patent: Jun. 20, 2017

(54) TRANSPORT OF POLARIZED LASER-RADIATION USING A HOLLOW-CORE FIBER

(71) Applicant: Coherent, Inc., Santa Clara, CA (US)

(72) Inventors: Michael Hertwig, San Ramon, CA (US); Norman Hodgson, Belmont, CA (US); Dmitri Simanovski, Palo Alto, CA (US)

(73) Assignee: Coherent, Inc., Santa Clara, CA (US)

( * ) Notice: Subject to any disclaimer, the term of this patent is extended or adjusted under 35 U.S.C. 154(b) by 0 days.

(21) Appl. No.: 15/098,103

(22) Filed: Apr. 13, 2016

(65) Prior Publication Data

US 2016/0334570 A1 Nov. 17, 2016

Related U.S. Application Data

(60) Provisional application No. 62/161,750, filed on May 14, 2015.

(51) Int. Cl.
| | |
|---|---|
| *G02B 6/02* | (2006.01) |
| *G02B 6/024* | (2006.01) |
| *G02B 6/27* | (2006.01) |
| *A61B 18/22* | (2006.01) |

(52) U.S. Cl.
CPC ......... *G02B 6/02304* (2013.01); *G02B 6/024* (2013.01); *G02B 6/2706* (2013.01); *G02B 6/2766* (2013.01); *A61B 2018/2227* (2013.01)

(58) Field of Classification Search
None
See application file for complete search history.

(56) References Cited

U.S. PATENT DOCUMENTS

| 2,403,731 | A | * | 7/1946 | MacNeille | G02B 27/142 |
|---|---|---|---|---|---|
| | | | | | 359/485.02 |
| 7,463,806 | B2 | | 12/2008 | Borrelli et al. | |
| 2005/0259942 | A1 | | 11/2005 | Temelkuran et al. | |
| 2007/0274623 | A1 | * | 11/2007 | Terrel | G02F 1/0136 |
| | | | | | 385/11 |
| 2015/0086148 | A1 | * | 3/2015 | Liu | G02F 1/3544 |
| | | | | | 385/1 |

FOREIGN PATENT DOCUMENTS

| GB | 2502142 A | 11/2013 |
|---|---|---|
| WO | 2007/103115 A2 | 9/2007 |

OTHER PUBLICATIONS

X. Chen et al. Generation of 4.3 fs, 1 mJ laser pulses via compression of circularly polarized pulses in a gas-filled hollow-core fiber. Optics Letters, 34:10:1588-1590, May 15, 2009.*
International Search Report and Written Opinion received for PCT Patent Application No. PCT/US2016/030531, mailed on Jul. 20, 2016, 11 pages.

* cited by examiner

*Primary Examiner* — Mike Stahl
(74) *Attorney, Agent, or Firm* — Morrison & Foerster LLP

(57) ABSTRACT

Plane-polarized laser-radiation from a laser-source is converted to circularly polarized radiation by a quarter-wave plate. The circularly polarized radiation is input into a hollow-core fiber for transport to a point of use. The transported radiation is converted back to plane-polarized radiation by another quarter-wave plate between the fiber and the point of use.

12 Claims, 5 Drawing Sheets

TRANSPORT OF POLARIZED LASER-RADIATION USING A HOLLOW-CORE FIBER

PRIORITY

This application claims priority to U.S. Provisional Patent Application Ser. No. 62/161,750, filed May 14, 2015, the disclosure of which is incorporated by reference in its entirety.

TECHNICAL FIELD OF THE INVENTION

The present invention relates in general to transporting laser radiation using an optical fiber. The invention relates in particular to transporting polarized, pulsed laser-radiation using a hollow-core (optical) fiber (HCF).

DISCUSSION OF BACKGROUND ART

Delivery (transport) fibers are commonly used to transport laser light (radiation) from a source thereof to a point of usage. This technique allows for a convenient separation of the source from the point of usage by many meters. State-of-the-art fiber delivery arrangements are able to transport continuous-wave (CW) laser radiation with powers of up to tens of kilowatts (kW) over distances of up to hundreds of meters. Such delivery arrangements typically employ a transport fiber having solid glass core surrounded by claddings and jackets to guide the radiation and protect the fiber.

When used with ultra-short pulsed, high-energy lasers, this solid glass core decreases the quality of the pulse in temporal and spectral domains due to nonlinear effects in the glass. This can lead to problems including an increased pulse-duration, and a severely distorted temporal pulse-profile (pulse-shape). In an extreme case of very high peak-power, for example about 5 megawatts (MW) or greater, the solid glass core of the delivery fiber can be destroyed.

A known solution to the problem is to substitute a hollow-core fiber (HCF) for the solid-glass-core fiber. A hollow-core fiber is a fiber in which radiation propagates primarily in a central hollow region surrounded by cladding material typically referred to as photonic crystal or photonic bandgap material. The photonic crystal material is surrounded by solid cladding material. Photonic crystal material is a mixture of solid (glass) and void regions (longitudinally-extending tubes) arranged in a particular pattern. Hollow-core fibers are commercially available from a number of suppliers and include types referred to as photonic bandgap fibers, Kagome lattice fibers, and anti-resonant fibers. FIG. 1, FIG. 2, and FIG. 3 are a cross-section micrographs schematically illustrating, respectively, examples of these three hollow-core fiber types.

In an HCF, the laser-radiation propagates primarily in air, some other gas, or vacuum, with only a small portion of radiation light propagating in glass. Because of this, the above-discussed nonlinear effects can be greatly decreased, and a high pulse-quality is maintained throughout the propagation in the fiber. This enables the transport of high energy picosecond (ps) and femtosecond (fs) pulses through the fiber with only minimal change to pulse-duration and pulse-shape.

In certain applications of pulsed laser-radiation, the radiation is delivered from a laser nominally plane-polarized in a preferred orientation, and it is desired that this polarization state is maintained at the point of usage after being transported thereto by a transport fiber. A particular challenge in the use of an HCF for laser-radiation transport is preserving (maintaining) the plane polarization of the laser-radiation during transport. It is possible to maintain the polarization orientation throughout the transport by carefully matching preferred polarization orientations of the HCF. Unfortunately, these orientations can rotate and change during operation, making realignment of the radiation-source and the HCF necessary. Parameters influencing the polarization-orientation include fiber temperature, temperature gradient, and fiber bending. Fiber bending limits substantially the use of an HCF for transporting plane-polarized radiation.

Moving the HCF or changing bending-planes will rotate and change the polarization state of the laser-radiation. In order to take advantage of an HCF for above described low-distortion transport of high-energy radiation pulses, a means is required for preserving plane-polarized radiation at an output of the fiber.

SUMMARY OF THE INVENTION

In one aspect, optical apparatus in accordance with the present invention comprises a source of plane-polarized laser-radiation. A hollow-core optical fiber is provided for transporting the radiation from the source to a point of use. The optical fiber has an input end and an output end. An optical element is located between the source and the input end of the optical fiber. The optical element is configured and arranged to convert the plane-polarized radiation to radiation which is otherwise polarized for transport through the optical fiber.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain principles of the present invention.

DETAILED DESCRIPTION OF THE INVENTION

Figure 1:
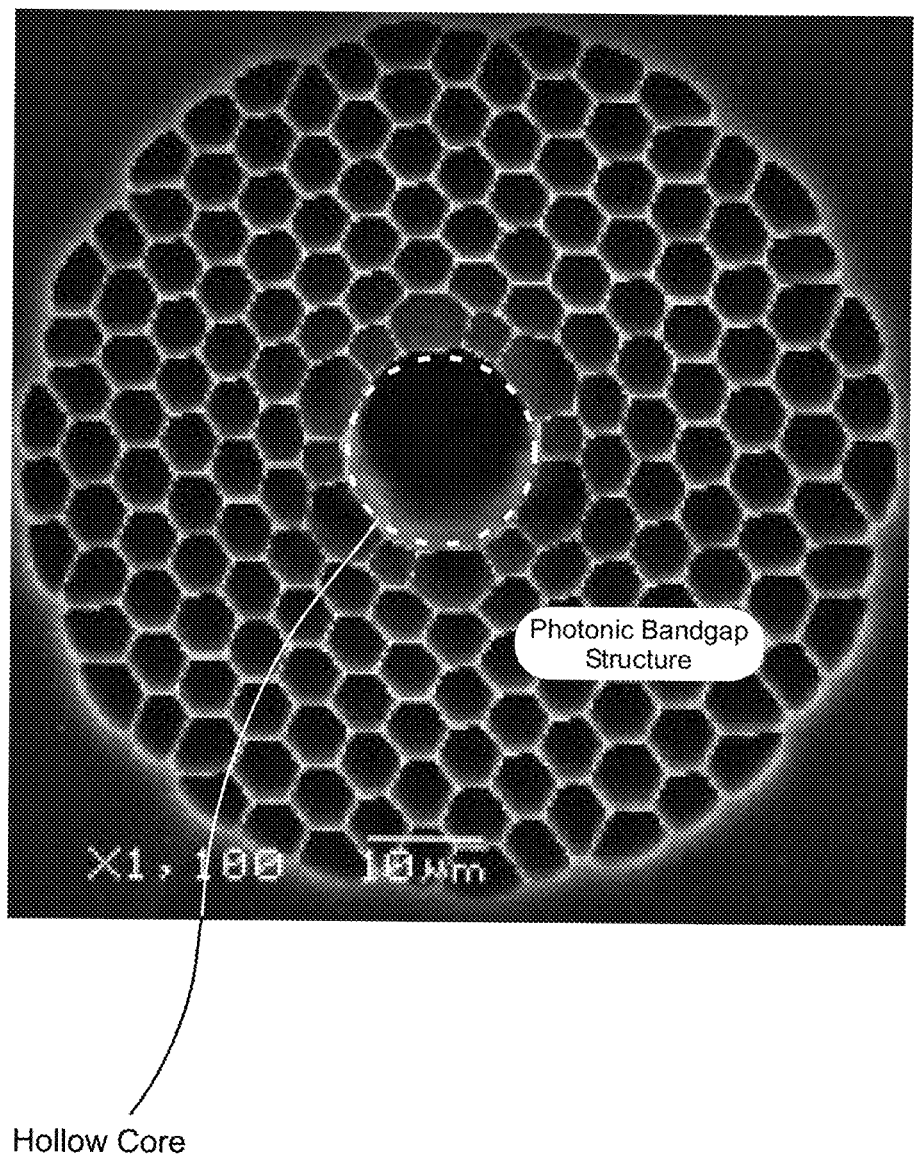
FIG. 1 is a cross-section micrograph schematically illustrating an example of a photonic-bandgap type hollow-core fiber.
Figure 2:
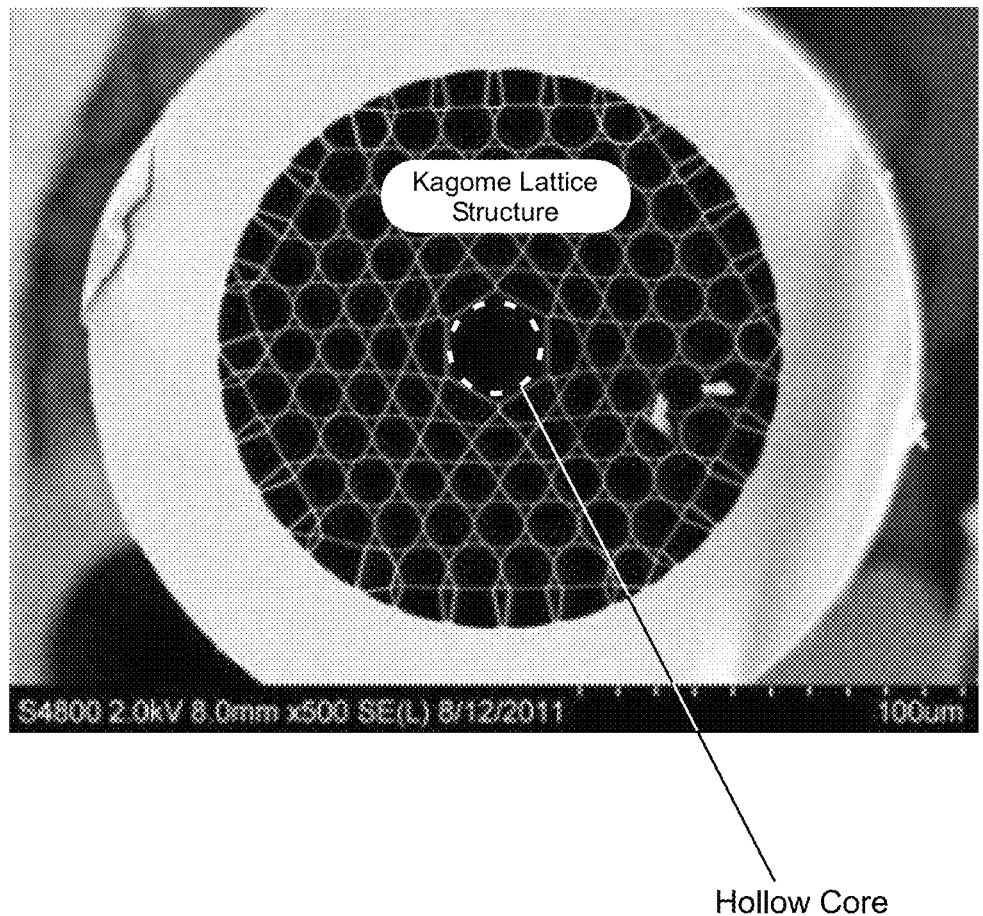
FIG. 2 is a cross-section micrograph schematically illustrating an example of a Kagomé lattice type hollow-core fiber.
Figure 3:
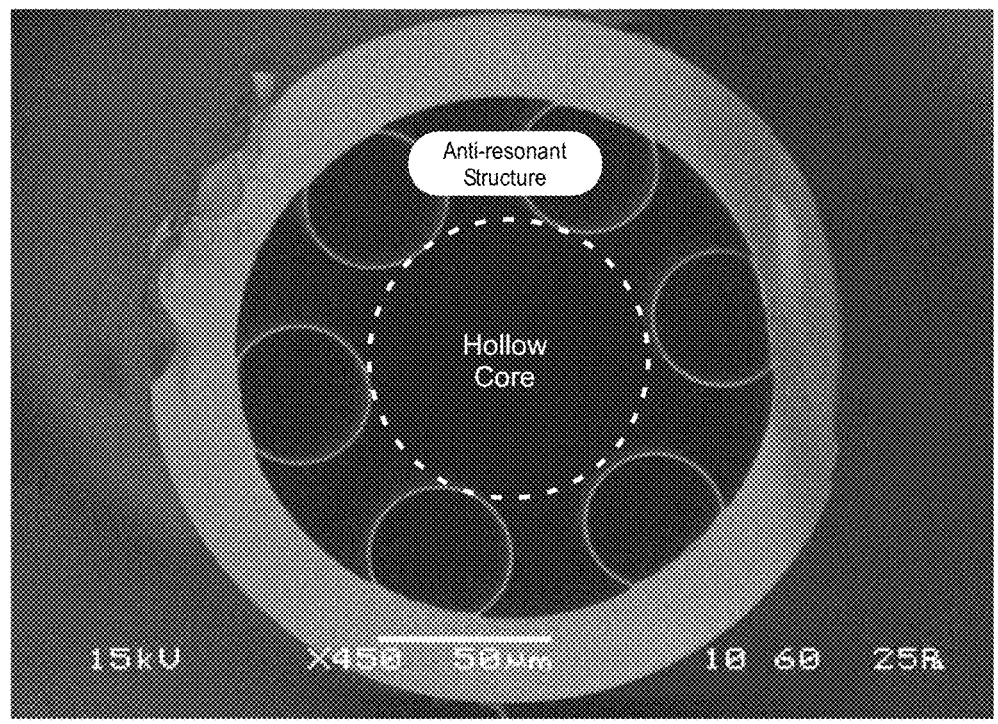
FIG. 3 is a cross-section micrograph schematically illustrating an example of an anti-resonant type hollow-core fiber.
Figure 4:
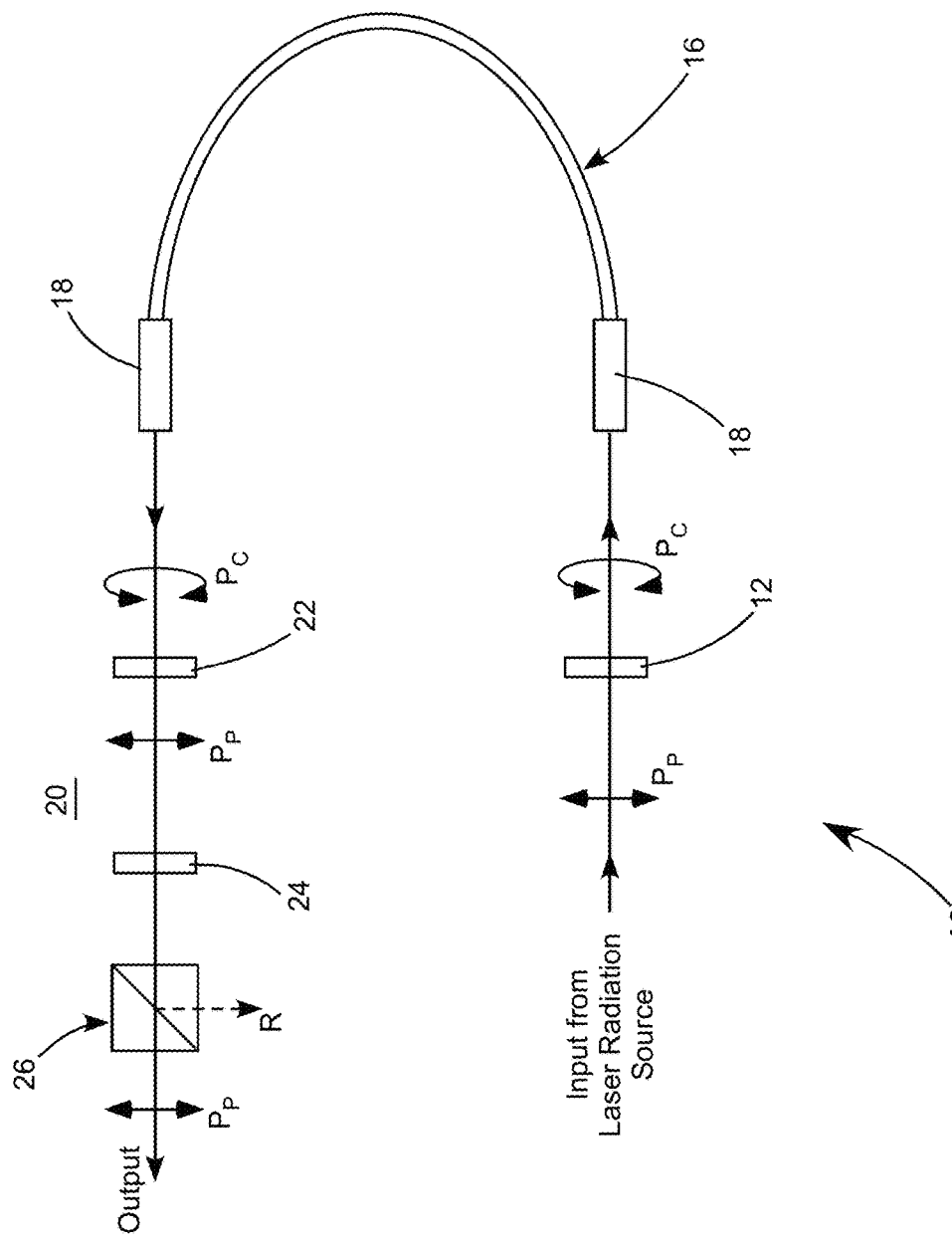
FIG. 4 schematically illustrates a preferred embodiment of apparatus in accordance with the present invention for transporting plane-polarized radiation to a location of use, including one quarter-wave plate for converting the plane-polarized radiation to circularly polarized radiation, a hollow-core fiber arranged to transport the circularly polarized radiation to the use-location, another quarter-wave plate at the use-location arranged to receive circularly polarized radiation from the hollow-core fiber and convert the circularly polarized radiation back to plane-polarized radiation, a polarizer, and a polarization-rotator arrange to rotate the plane of the back-converted plane-polarized radiation to an orientation which will be maximally transmitted by the polarizer.

Turning now to the drawings, FIG. 4 schematically illustrates a preferred embodiment 10 of apparatus in accordance with the present invention for transporting plane-polarized radiation from a source thereof to a location of use. Plane-polarized radiation from the source is transmitted through quarter-wave plate 12, which converts the plane-polarized radiation, preferably, to circularly polarized radiation.

A hollow-core fiber (HCF) 16, here, terminated at each end thereof by ferrules 18, is arranged to transport the circularly polarized radiation to the use-location 20. Circularly polarized radiation exiting HCF 16 is transmitted through a quarter-wave plate 22 at the use-location. Quarter-wave plate 22 is arranged to convert the circularly polarized radiation from the hollow-core fiber back to nominally plane-polarized radiation.

The plane-polarized radiation delivered from quarter-wave plate 22 may have a lesser degree of plane-polarization (extinction-ratio), and a somewhat different polarization-orientation, than that of the plane-polarized radiation from the source thereof. This would be due to artifacts introduced by the HCF due to bends, stress, imperfections and the like. Accordingly, the radiation transmitted by quarter-wave plate 22 is transmitted first through a polarization-rotator 24, such as a half-wave plate, and then through a polarizer 26, here, a polarization-selective reflector in the form of a MacNeille bi-prism. Polarization-rotator 24 is arranged to rotate the plane of the back-converted plane-polarized radiation to an orientation which will be maximally transmitted by polarizer 26. The polarizer rejects any residual otherwise-polarized components of the nominally plane-polarized radiation as indicated by arrow R.

It should be noted here that while HCF 16 is depicted in FIG. 4 as being relatively short in practice, the HCF will typically have a length of several meters (m). In prior-art arrangements, wherein plane-polarized light is directed into an HCF without a change of polarization state, and exits the HCF plane-polarized but in an unpredictable orientation, a half-wave plate could be rotated to maximize transmission through the polarizer, i.e., to align the polarization-orientation of delivered radiation with that defined by the polarizer. However, factors such as movement of the fiber in use, or change in temperature of the fiber in use will change the orientation (rotation) of the output plane-polarization resulting in fluctuation of the polarizer output. In the inventive apparatus of FIG. 4, the orientation of plane-polarized radiation delivered to half-wave plate 24 is determined primarily by quarter-wave plate 22.

Figure 5:
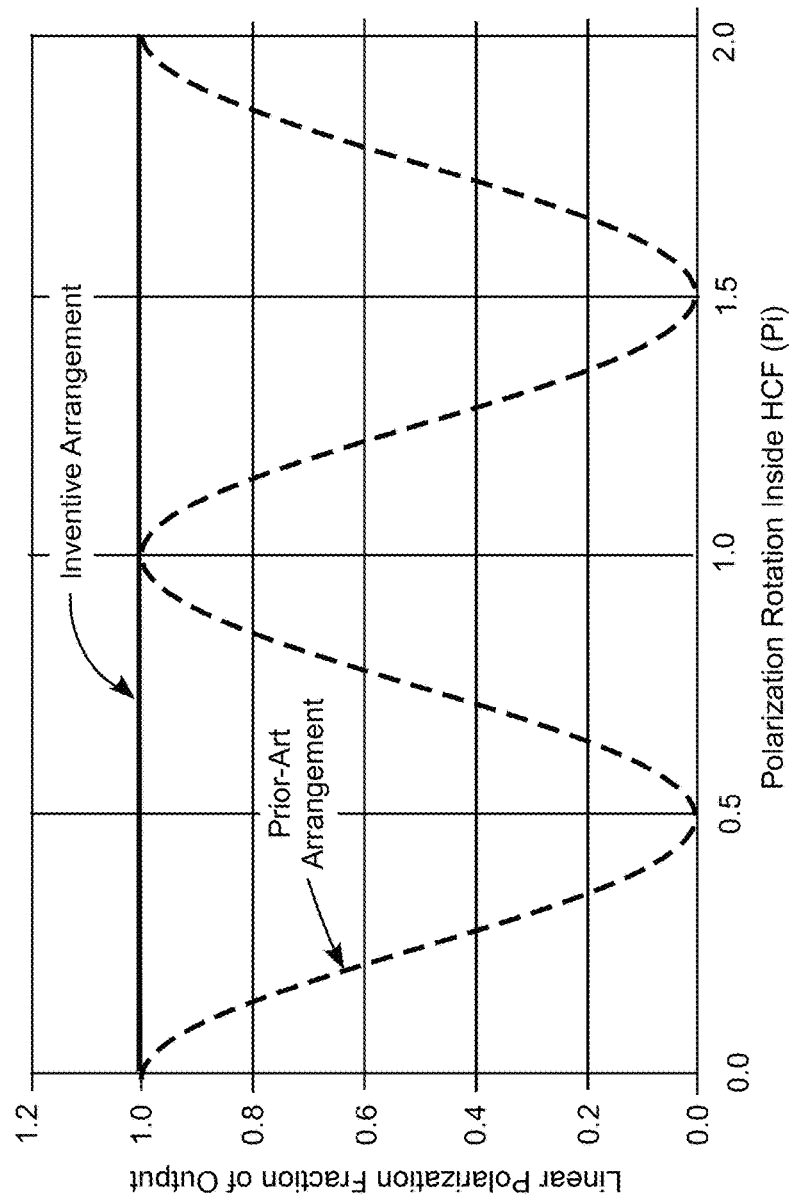
FIG. 5 is a graph schematically illustrating calculated fraction of radiation transmitted by the polarizer of FIG. 4 as a function of polarization-rotation introduced in the radiation by the hollow-core fiber, with and without the polarization-converting quarter-wave plates and polarization-rotator of the present invention.

FIG. 5 is a graph schematically illustrating calculated normalized transmission of polarizer 26 as a function of polarization rotation in HCF 16 for the inventive arrangement of FIG. 4 (solid curve), and for a prior-art arrangement in which quarter-wave plates 12 and 22 are omitted, and plane-polarized radiation is directed into, and delivered from the HCF (dashed curve). It is assumed that half-wave plate 24 is initially adjusted (at zero rotation) for maximum transmission through the polarizer and not readjusted as polarization-rotation by the HCF changes. It can be seen that for the prior-art case, transmission drops from 100% to zero for a change in polarization-rotation of only 0.5Pi ($\pi/2$). This is not an unlikely occurrence in an HCF several meters in length. For the inventive arrangement the calculated transmission remains the same regardless of polarization-rotation.

In experiments with the inventive arrangement, a Kagomé lattice type HCF was employed having a hollow-core diameter of about 55 micrometers ($\mu$m) and a length of about 3 meters. The HCF was coiled into diameters ranging between 50 centimeters (cm) and 100 cm. With circularly polarized radiation launched into the fiber as depicted in FIG. 4, it was found that movement of the fiber caused output of the polarizer to vary between a maximum and about 85% of that maximum value.

It should be noted here that while conversion of the plane-polarized light to circularly polarized light is described above, the plane-polarized light can be converted to some other polarization state which is not plane-polarized (otherwise polarized). If the radiation transported by the fiber can be used without re-conversion to plane-polarization, then the plane-polarization can be converted to any state which can be transported by the HCF and is relatively insensitive to changes in fiber-bending, fiber-temperature or temperature-gradients. Such states include circularly polarized, elliptically polarized, and azimuthally polarized. Circularly and elliptically polarized radiation is readily converted back to plane polarized radiation by a second fractional-wave plate, as discussed above.

Further, it should be noted that the term plane-polarized should not be construed as meaning precisely plane-polarized. In general all radiation that is nominally plane-polarized in one direction may include a relatively small amount of some component that is polarized at 90 degrees to that direction. The ratio of that component to the nominal component is referred to by practitioners of the art as the extinction ratio. In the above scheme, the nominally plane polarized radiation preferably has an extinction ratio no greater than about $10^{-1}$ and more preferably no greater than about $10^{-2}$.

The present invention is described above in terms of a preferred and other embodiments. The invention is not limited however to the embodiments described and depicted. Rather the invention is limited only by the claims appended hereto.

What is claimed is:

1. An optical apparatus, comprising:
    a source of plane-polarized laser-radiation;
    a hollow-core optical fiber for transporting the radiation from the source to a point of use, the optical fiber having an input end and an output end;
    a first optical element between the source and the input end of the optical fiber, the element configured and arranged to convert the plane-polarized radiation to radiation which is otherwise polarized for transport through the optical fiber;
    a second optical element between the output end of the optical fiber and the point of use, the second optical element configured to convert the otherwise-polarized, transported radiation back to plane-polarized radiation: and
    a polarization rotator between the second optical element and the point of use, for rotating the polarization plane of the converted plane-polarized radiation to a desired polarization plane.

2. The apparatus of claim 1, wherein the otherwise-polarized radiation is one of circularly polarized and elliptically polarized.

3. The apparatus of claim 1, further including a polarizer between the polarization rotator and the point of use.

4. The apparatus of claim 3, wherein the polarization rotator is a half-wave plate and the polarizer is a polarization-selective reflector.

5. The apparatus of claim 4, wherein, the polarization-selective reflector is a MacNeille bi-prism.

6. The apparatus of claim 1, wherein the hollow-core fiber is one of a photonic-bandgap type, a Kagome lattice type, and an anti-resonant type.

7. An optical apparatus, comprising:
a source of plane-polarized laser-radiation;
a hollow-core optical fiber for transporting the radiation from the source to a point of use, the optical fiber having an input end and an output end;
a first optical element between the source and the input end of the optical fiber, the element configured and arranged to convert the plane-polarized radiation to elliptically polarized laser radiation for transport through the optical fiber;
a quarter-wave plate positioned near the output end of the fiber to convert the elliptically polarized laser radiation back to plane-polarized laser radiation;
a polarization rotator positioned to receive the converted plane-polarized laser radiation; and
a polarizer positioned to receive the laser radiation transmitted through the polarization rotator.

8. The apparatus of claim 7, wherein the elliptically polarized radiation is substantially circularly polarized.

9. The apparatus of claim 7, wherein the polarization rotator is a half-wave plate.

10. The apparatus of claim 9 wherein the polarizer is a polarization-selective reflector.

11. The apparatus of claim 10, wherein, the polarization-selective reflector is a MacNeille bi-prism.

12. The apparatus of claim 7, wherein the hollow-core fiber is one of a photonic-bandgap type, a Kagome lattice type, and an anti-resonant type.

\* \* \* \* \*